United States Patent [19]

D'Silva

[11] Patent Number: 5,762,867
[45] Date of Patent: Jun. 9, 1998

[54] APPARATUS AND METHOD FOR ACTIVATING PHOTOACTIVE AGENTS

[75] Inventor: Edmund D. D'Silva, Vernon Hills, Ill.

[73] Assignee: Baxter International Inc., Deerfield, Ill.

[21] Appl. No.: 299,398

[22] Filed: Sep. 1, 1994

[51] Int. Cl.[6] .................................................. A61M 1/36
[52] U.S. Cl. .................... 422/44; 422/23; 250/455.11; 362/294; 435/2; 604/4
[58] Field of Search .................... 422/186, 23, 44; 250/455.11; 362/800, 373, 294; 435/2; 313/12, 23, 28, 32, 35, 36, 40; 604/4, 20

[56] References Cited

U.S. PATENT DOCUMENTS

| | | |
|---|---|---|
| 4,573,961 | 3/1986 | King . |
| 4,573,962 | 3/1986 | Troutner . |
| 4,683,889 | 8/1987 | Edelson . |
| 4,705,498 | 11/1987 | Goss . |
| 4,708,715 | 11/1987 | Troutner et al. . |
| 4,866,282 | 9/1989 | Miripol et al. ............... 250/455.11 |
| 4,878,891 | 11/1989 | Judy et al. ..................... 604/5 |
| 5,171,749 | 12/1992 | Levy et al. ..................... 514/410 |
| 5,278,432 | 1/1994 | Ignatius et al. . |
| 5,290,221 | 3/1994 | Wolf, Jr. et al. .............. 604/4 |
| 5,301,090 | 4/1994 | Hed ................................ 362/32 |

*Primary Examiner*—Robert J. Warden
*Assistant Examiner*—Elizabeth Dawson
*Attorney, Agent, or Firm*—Robert M. Barrett; Denise M. Serewicz; Bradford R. L. Price

[57] ABSTRACT

The present invention provides improved methods and apparatus for irradiating a product with light of a specific wavelength to activate the photoactive agent that is contained therein. To this end, in an embodiment, a device is provided that comprises a source of radiation including a plurality of light emitting diodes. Each light emitting diode includes a body portion through which radiation is transmitted. The body of the diode is surrounded by a fluid. In this regard, a first housing is provided that includes an interior that contains the light emitting diodes and a fluid. The housing includes a transparent window for allowing radiation generated by the light emitting diodes to flow through the window and irradiate a product that is in juxtaposition to the window.

19 Claims, 2 Drawing Sheets ature rated around 100° C. If the junction temperature
5,762,867

APPARATUS AND METHOD FOR ACTIVATING PHOTOACTIVE AGENTS

BACKGROUND OF THE INVENTION

The present invention relates generally to medical devices and methods and apparatuses for treating individuals. More specifically, the present invention relates to apparatuses and methods for utilizing photoactive compounds to inactivate contaminants in body fluids.

In a wide variety of therapies, such as transfusions and transplants, body fluids, especially blood components such as red blood cells, platelets, plasma, and bone marrow, are infused from one or more individuals into a patient. Although such therapies provide treatments, many of which are life saving and cannot otherwise be provided, due to the transmission of infectious diseases, there may be a potential risk to such therapies.

For example, it is known that blood can carry infectious agents such as hepatitis virus, human immune deficiency virus (HIV), cytomegalovirus, Epstein Barr virus, and herpes virus. Although screening methods exist to identify blood that may include such viruses, current screening methods do not insure that every blood unit that contains such a virus is identified.

For example, in this regard, one of the difficulties in testing blood components for viral contamination, such as HIV, is that many current diagnostic tests are based on an identification of antibodies. Therefore, a contaminated blood component will only exhibit a positive test if it includes antibodies for the virus, e.g., anti-HIV.

With respect to intracellular viral infections, an individual may not generate the antibodies immediately upon infection. Rather, there is a window period that extends from the initial infection of the patient with the virus to the generation of antibodies. When an individual is in this window period, diagnostics tests that are based on antibodies will not identify the individual, or the blood unit, as being infected. But, even though antibodies are not present, the blood unit can still transmit an infection.

With respect to HIV infection, it is believed that this window period can extend from approximately six weeks up to many months. During this time period, the individual who has been infected with HIV and accordingly, whose blood will transmit same, will register a negative antibody response. Typically used blood screening methods will not identify a contaminated blood unit from an individual who is infected with HIV but who has not generated anti-HIV.

In order to address the limitations of typical diagnostic techniques and also deal with the concern of transmission of viral contaminants and other pathogens to a patient receiving a transfusion, recent attention has focussed on the development of viral inactivating agents. It is envisioned that these viral inactivation agents would be added to the body fluid prior to the body fluid being administered to the patient.

For example, a number of photoactive agents that have antiviral action have been explored. These photoactive agents are generally agents that upon activation with light will inactivate or destroy pathogens, e.g., a virus that may be present. Such photoactive agents include: psoralens; porphyrins; phthalocyanines; and dyes such as methylene blue. See, for example, U.S. Pat. Nos.: 4,748,120; 4,878,891; 5,120,649; and German Patent Application No. DE 39 30 510 A1 (Mohr).

Although much effort has been focussed on commercializing such methods using photoactive agents, the inventors believe that such methods are currently not commercially viable. It is believed that such a system for utilizing a photoactive agent to treat blood to irradiate or remove viral and other contaminants would entail combining the blood with a photoactive agent in a container and irradiating the resultant mixture with light of the appropriate wavelength.

A number of devices and methods have been postulated for use in adding and activating photoactive agents in a body fluid.

U.S. patent application Ser. No. 08/090,381 entitled: "APPARATUS AND METHOD FOR INACTIVATING VIRAL CONTAMINANTS" filed on Jul. 12, 1993 discloses an apparatus and method for inactivating viral contaminants in body fluids. In an embodiment of the invention, a method for inactivating viruses is provided comprising the steps of forming a mixture including a therapeutically effective amount of methylene blue and an amount of a body fluid in a container under sterile conditions. The mixture is irradiated with a light field of a suitable intensity and wavelength for activating the methylene blue for a time sufficient to inactivate viruses in the mixture. During the process, the mixture is maintained in a substantially static state within the container. The apparatus includes a light source that is disposed along a path of travel and configured to generate a light field over the path of travel with a frequency suitable for activating the photoactive agent. In an embodiment, light emitting diodes are mounted on a printed circuit board. Two arrays are mounted facing each other in a spaced apart relationship so that a gap is presented within which the container containing the body fluid can pass.

U.S. patent application Ser. No. 08/174,211 entitled: "SYSTEMS AND METHODS FOR IRRADICATING CONTAMINANTS USING PHOTOACTIVE MATERIALS AND FLUID LIKE BLOOD USING DISCRETE SOURCES OF RADIATION," filed Dec. 28, 1993, discloses, in an embodiment, a system for treating a fluid carrying a contaminant to which a photoactive material has been bound. The system directs fluid through a treatment chamber in a predetermined flow path. The system establishes at least two discrete sources of radiation in a flow path at spaced apart locations along the direction of fluid flow.

Other systems and apparatuses for treating a fluid with a photoactive material are disclosed in U.S. Pat. Nos. 5,300,019 and 5,290,221, as well as U.S. patent application Ser. No. 08/289,175 filed Aug. 11, 1994 entitled: "SYSTEMS AND METHODS FOR SIMULTANEOUSLY REMOVING FREE AND ENTRAINED CONTAMINANTS IN FLUID LIKE BLOOD USING PHOTOACTIVE THERAPY AND CELLULAR SEPARATION TECHNIQUES," and now U.S. Pat. No. 5,536,238, which is a continuation of U.S. Ser. No. 07/630,864. Additionally, U.S. Pat. No. 5,278,432 discloses an apparatus for providing radiant energy.

One of the difficulties, however, in using light emitting diodes for activating a photoactive compound is that the light emitting diodes will burn out if they overheat. In this regard, most light emitting diodes (LEDs) have a junction temperature rated around 100° C. If the junction temperature exceeds 100° C., the light emitting diode will burn out. A problem arises because the greater the intensity of light that is generated the greater the temperature of the LEDs. Thus, heretofore, one had to sacrifice efficiency and cycle time in proposed light activating systems to prevent LED burnout.

There therefore is a need for an improved system and method for activating photoactive agents.

SUMMARY OF THE INVENTION

The present invention provides improved methods and apparatus for irradiating a product with light of a specific wavelength to activate the photoactive agent that is contained therein.

To this end, in an embodiment, a device is provided that comprises a source of radiation including a plurality of light emitting diodes. Each light emitting diode includes a body portion through which radiation is transmitted. The body of the diode is surrounded by a fluid. In this regard, a first housing is provided that includes an interior that contains the light emitting diodes and a fluid. The housing includes a transparent window for allowing radiation generated by the light emitting diodes to flow through the window and irradiate a product that is in juxtaposition to the window.

In an embodiment, the device includes a body for supporting the housing and an opening for allowing the product to be placed in juxtaposition to the window and removed from same.

In another embodiment, the device includes a second housing for enclosing a second plurality of light emitting diodes, the second housing including a transparent window. In an embodiment, the first housing and second housing are located in planes that are substantially parallel to each other.

In an embodiment, the housing includes an inlet for allowing fluid to flow into the interior and an outlet for allowing fluid to flow out of the interior. Preferably, the inlet and outlet are connected to fluid conduits and a pump is provided to pump fluid through a first fluid conduit into the inlet. Preferably, the device includes means for cooling fluid before it enters the fluid inlet.

In an embodiment, the fluid is chosen from the group consisting of: distilled water; propylene glycol containing fluids; and oil based fluids.

In an embodiment, the refractive index of the fluid is greater than the refractive index of the body of the LED.

In an embodiment, the refractive index of the fluid is less than the refractive index of the body of the LED.

In another embodiment, the present invention provides a system for irradiating a container including a fluid that includes a photoactive agent. The system comprises a housing including an interior for receiving a container and a first and second photodiode device. Each photodiode device includes a body defining a chamber that includes a plurality of photodiodes for generating radiation of a specific wavelength. Each chamber includes a fluid therein for cooling the photodiodes. The first and second photodiode devices are located in planes that are substantially parallel to each other and define a space therebetween in the interior for receiving the container. The housing includes an opening for allowing the container to be placed within the space and removed therefrom.

In a further embodiment, the present invention provides a system for irradiating a container including a fluid that includes a photoactive agent. The system comprises a housing including an interior for receiving a container, and a photodiode device including a body that includes a plurality of photodiodes for generating radiation of a specific wavelength. The chamber includes an inlet for receiving a fluid therein for cooling the photodiodes. The body includes a transparent window that supports the container when it is placed in the interior. The system includes means for cooling fluid prior to the fluid entering the inlet.

In another embodiment of the present invention, a method for irradiating a product with light of a specific wavelength is provided. The method comprises the steps of: providing a device including an interior for receiving a product, the device including a chamber including a plurality of photodiodes and a fluid; placing the container in the device; and irradiating the product with light of a specific wavelength.

In a further embodiment, pursuant to the present invention, a method for inactivating viral contaminants in blood comprising the steps of: adding a photoactive agent to a blood component; providing a device including an interior for receiving a product, the device including a chamber including a plurality of photodiodes; cooling the photodiodes using a fluid; placing the container in the device; and irradiating the product with light of a specific wavelength.

In an embodiment of the method, the intensity of the light is varied by choosing a fluid having a desired refractive index.

An advantage of the present invention is to provide an improved apparatus for activating photoactive agents that may be contained in a fluid.

A further advantage of the present invention is that it provides an improved method for activating a photoactive agent that may be contained in a fluid.

Moreover, an advantage of the present invention is to provide an improved method for treating a body fluid to at least substantially inactivate viral contaminants that may be contained therein.

Furthermore, an advantage of the present invention is that it provides a method for inactivating or eliminating pathogens from blood or its components before they are infused into a patient.

Still further, an advantage of the present invention is that it provides an apparatus and method that allows light emitting diodes to be operated at a higher intensity than theretofore possible without burning out.

Another advantage of the present invention is that it provides a method for varying the intensity of light that is provided by an array of light emitting diodes.

Further, an advantage of the present invention is that it provides an economical method for cooling light emitting diodes.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an apparatus, as well as a method, for activating photoactive agents that are contained in a product. In the preferred embodiment discussed herein, the present invention is directed to activating photoactive agents that are added to a body fluid, such as blood or a blood component. Such blood components include red blood cells, platelets, plasma, leukocytes, and bone marrow. These products are typically housed in flexible plastic containers constructed from, for example, polyvinyl chloride. Such containers are available from Baxter International Inc. as well as other companies.

Although in the preferred embodiment the present invention is directed to activating photoactive agents that are added to a body fluid such as blood or its components, it should be appreciated that the present invention can be used in a variety of other applications. In this regard, the present invention provides an improved method and apparatus for generating light of a specific wavelength.

Currently, much research is being conducted in utilizing photoactive agents to inactive viral contaminants that may be present in a body fluid. A variety of photoactive agents have been proposed and can be used pursuant to the present invention. For example, the photoactive agents can be chosen from the group including, but not limited to: porphyrins; porphyrin derivatives; merocyanines, such as MC540; phthalocyanines, such as aluminum phthalocyanine; other pyrrolic macrocycles; psoralens; and other photoactive dye stuffs, such as methylene blue. It is believed the present invention can be used with any photoactive agent. What is required is that the LEDs, or other light source of the present invention, must be modified so that it generates light of an appropriate wavelength. As stated above, photoactive agents are activated by light of a specific wavelength.

Likewise, the present invention can be utilized with any method for adding the photoactive agent to the body fluid. For example, the photoactive agent can be added to the body fluid contained in the source container after the blood is collected from a donor. An example of a method and apparatus that can be used for adding photoactive agents to a body fluid is set forth in U.S. patent application Ser. No. 07/952,427 entitled: "STEAM STERILIZABLE SYSTEM FOR INACTIVATING VIRAL CONTAMINANTS IN BODY FLUIDS", filed Oct. 5, 1992, the disclosure of which is incorporated herein by reference. In that application, in an embodiment, methylene blue is added to a body fluid. However, other methods can be utilized pursuant to the present invention for adding photoactive agents to a body fluid.

Figure 1:
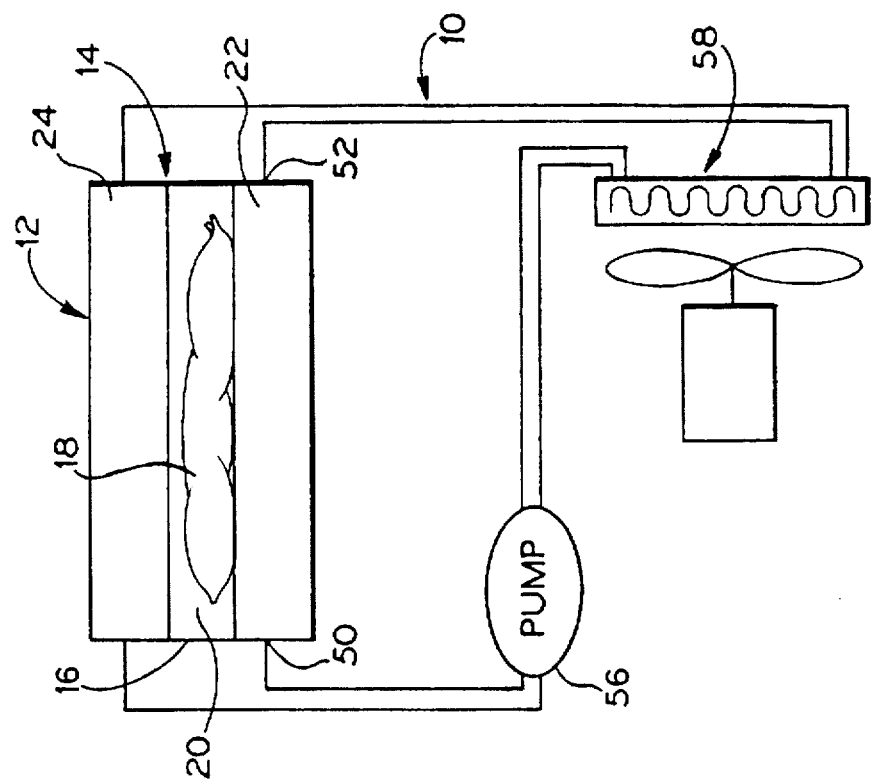
FIG. 1 illustrates a schematic view of an apparatus of the present invention.

Referring now to FIG. 1, generally a system 10 including an apparatus 12 is illustrated for activating a photoactive agent present in a body fluid that is housed in a container. The apparatus 12 includes a housing 14 that has an opening 16 for allowing a product 18, e.g., a bag containing blood and a photoactive agent, to be received within a chamber 20. In an embodiment, the housing 14 includes a drawer (not illustrated) having a handle that allows one to access the opening 16 to place the product 18 within the chamber 20 and close same. However, a variety of other means can be utilized to access the chamber 20 of the housing 14.

Figure 2:
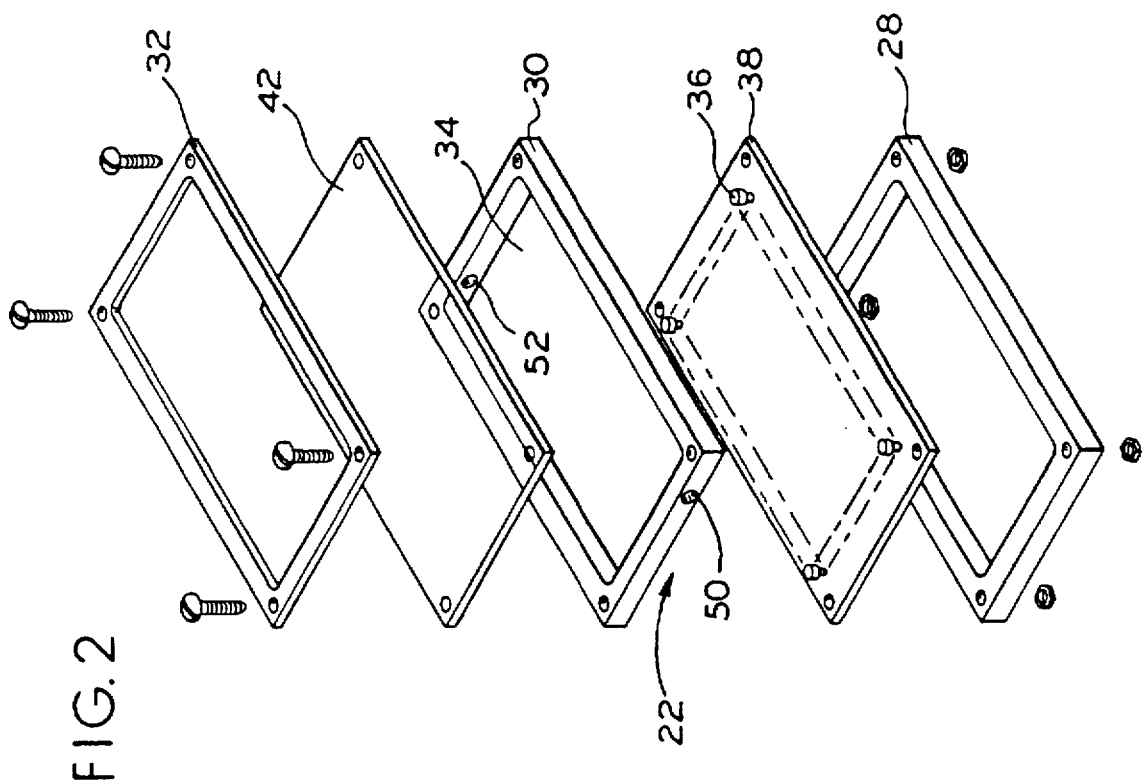
FIG. 2 illustrates an exploded view of a light emitting diode (LED) unit of the apparatus for irradiating a container of FIG. 1.

Located within the housing 14 are, in the preferred embodiment illustrated, two light emitting diodes (LED) devices 22 and 24. FIG. 2 illustrates an exploded view of one of the LED devices 22. The LED devices 22 and 24 are constructed and arranged so as to generate light of an appropriate wavelength to activate the photoactive agent contained within the container 18. Because the container (bag) 18 is transparent, the light will be transmitted through the bag into the body fluid activating the photoactive agent contained therein.

Figure 3:
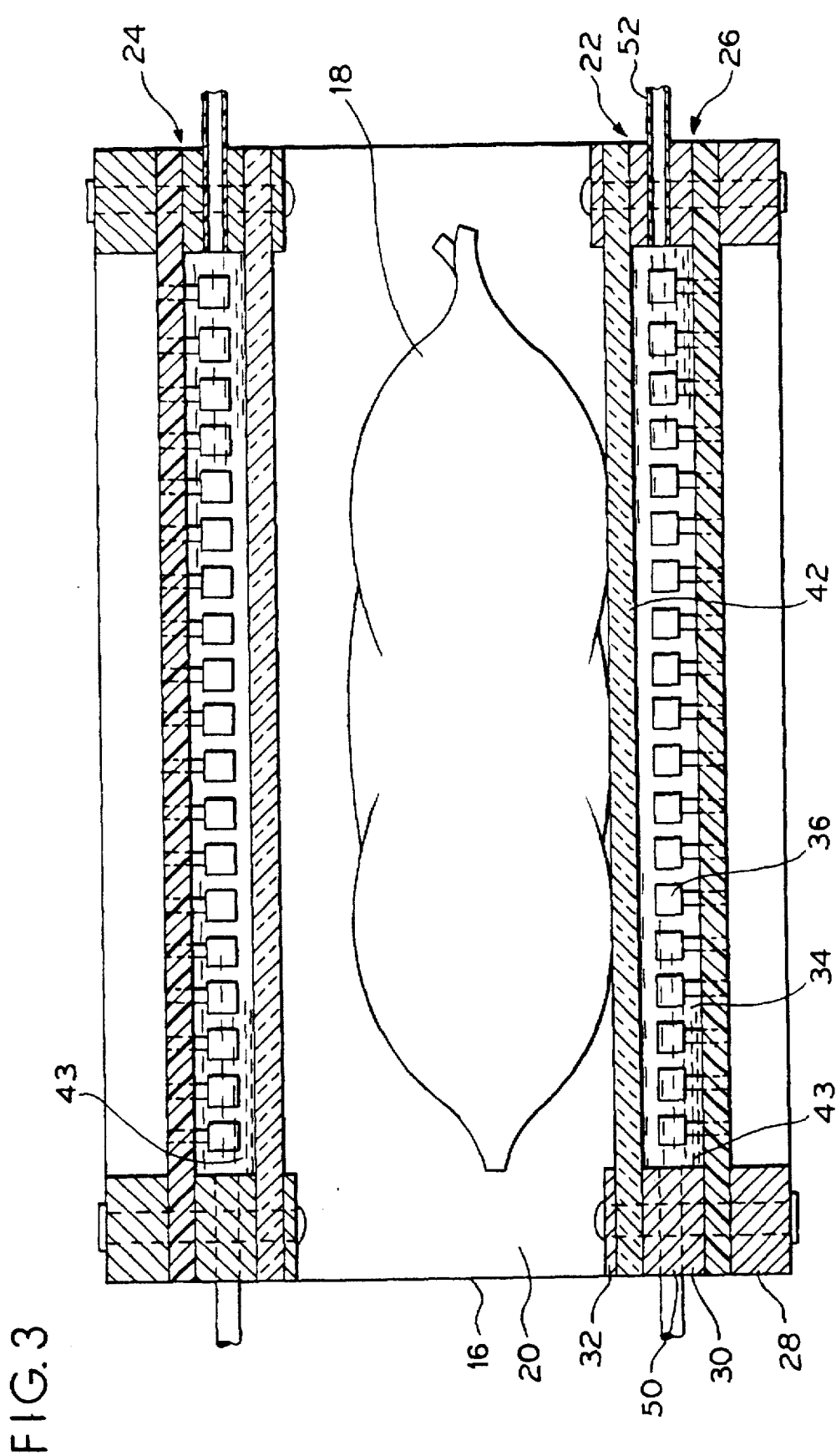
FIG. 3 illustrates a cross-sectional view of the apparatus for irradiating a container of FIG. 1.

As illustrated in FIGS. 2 and 3, each of the LED devices 22 and 24 includes a housing 26. In the embodiment illustrated, the housing 26 includes three structures that define the housing. In this regard, there is a lower frame 28, a middle frame 30, and an upper frame 32. The frames 28, 30, and 32 define the housing 26 that contains the LEDs therein. The frames can be constructed from a variety of materials. In a preferred embodiment, the upper and lower frames 28 and 32 are constructed from stainless steel and the middle frame 30 from plastic.

The housing 26 defines an interior 34 for containing the LEDs 36. Preferably, the LEDs 36 are located on an LED board 38. This board 38 is connected to a cable (not shown) to power the LEDs 36. Such a connection is known in the art. Preferably, the LEDs 36 are mounted so that they are not flush with the board 38. To this end, each LED 36 has two electrodes coming out of the bottom which are mounted to the board 38. The LEDs 36 are arranged on the board 38 in rows or arrays. Depending on space and the size of the product, a variety of different LED arrays can be used.

By way of example, the LEDs 36 can comprise any of a variety of LEDs including those available from: Hewlett Packard; Marktech; and Gilway. For example, for treating red blood cells, it may be desirable to use photodiodes available from Hewlett Packard under the designation HLMP-8150 15 candela. These photodiodes use transparent substrate aluminum gallium arsenide material (TsAlGaAs). These photodiodes emit a band of radiation at a relatively narrow viewing angle of about 4 degrees. The prescribed band of radiation has a relatively precise wavelength displaying a red color having a peak wavelength of about 660 nm. Red blood cells are essentially transparent to radiation at this wavelength. However, the photoactive agent benzoporphyrin is not and if contained in a container with red blood cells will be activated. Of course, depending on the photoactive agent and type of fluid, different LEDs 36 will be used.

As illustrated, each of the LED devices 22 and 24 includes a transparent window 42. The transparent window 42 allows radiation from the LEDs 36 to enter the chamber of the apparatus. In the preferred embodiment illustrated, the transparent window 42 supports the container 18 within the apparatus. A number of materials can be used to construct the window 42. In a preferred embodiment, the window 42 is constructed from polycarbonate plastic.

Pursuant to the present invention, the LEDs 36 are cooled by a fluid 43. The fluid 43 removes the heat from the LEDs 36. In the preferred embodiment illustrated, the fluid 43 is trapped in the interior 34 between the LED board 38 and the middle frame 30 and the clear window 42 which is located between the upper 32 and middle frame 30.

Although the fluid 43 is passed over the top of the LED board 38, if desired, however, the entire board, top and bottom, can be located within the fluid.

To allow the fluid 43 to flow through the interior 34 defined by the middle frame 30, the LED board 38, and the clear window 42, an inlet port 50 and an outlet port 52 are provided. This allows the fluid 43 to be circulated and cooled. The cooling of the fluid 43 will be discussed hereinafter.

A number of different fluids can be used in the present invention. Preferably, the fluid 43 is chosen from the group consisting of: distilled water; propylene glycol based fluids; and oil based fluids. Examples of such fluid are Dow Frost from Dow Chemical, Calflow LT from Petro Canada, and Paratherm NF from Paratherm Corporation.

Any fluid that does not conduct electricity can be used in the present invention. In choosing the fluid, one needs to insure that the fluid is not and does not become contaminated. Contaminated fluid will then conduct electricity.

Pursuant to the present invention, the LEDs 36 are cooled so that they do not experience a temperature change of greater than 10°. For example, if the room temperature is 25° C., the fluid 43 should insure that the LEDs 36 will not be heated to a temperature of greater than 35° C. This will provide a junction temperature for the LEDs of 50° C. or less. Because LEDs are rated at a junction temperature of around 100° C., at such a temperature, the LEDs will not fail.

Preferably, the fluid 43 flows into the inlet port 50 and, therefore, into the interior 34 of the LED device 22, at ambient temperature. However, if desired, the temperature of the fluid 43 can be lower or higher than ambient temperature.

Preferably, the fluid 43 fills the entire interior 34 of the LED device 22. This is desirable so that no air bubbles are present that would affect the refractive index of the fluid.

Referring now to FIG. 1, preferably, the system 10 of the present invention includes a pump 56 for pumping fluid into the inlet ports 50 of the LED devices 22 and 24 and thereby out of the outlet ports of the devices. In the illustrated embodiment of the system 10, a heat exchanger/thermal electric cooler 58 is also provided to cool the fluid after it has left the LED device. A variety of heat exchanger/thermal electric coolers 58 can be used. It is believed it is only necessary to cool the fluid down to ambient conditions.

Due to the use of the fluid 43, heat can be removed from the LEDs 36 allowing the LEDs to run at a higher intensity. For example, manufacturers recommend that typical LEDs 36 run at a maximum of 50 milliamps. However, utilizing the fluid 43 of the present invention, the LEDs 26 can be run at 90 milliamps for extended periods of time. This is due to the fact that so much heat is removed by the fluid 43.

A further advantage of the present invention is that in addition to cooling the LEDs 36 with fluid, the intensity of the light generated by the LED can be varied by the fluid. The angle of light generated by the LED and its brightness is originally dependent on the type of LEDs. By choosing a liquid that has a refractive index higher or lower than the material from which the LED is created, one can change the intensity of light.

For example, the refractive index of plastic that is used for the body of some LEDs 36 is approximately 1.6. If one chooses a refractive index that is less than 1.6, the angle of the light will be less and therefore, the light will be more intense. If one picks a fluid with a refractive index that is higher than 1.6, this will increase the angle of the light and make the light less intense.

Therefore, if one wants brighter light in certain areas during the photoactivation process, by selecting the appropriate fluid, one can increase the intensity of light in certain areas. In a similar vein, if one wants a broad illumination, this can be accomplished by choosing a fluid that has a refractive index that is greater than the material from which the LED is manufactured.

It is believed that one will probably want to increase the power (brightness) of the light generated by the LEDs so that the radiation of the fluid can be accomplished much cheaper and reduce the cycle time. Therefore, it is envisioned that one will choose a fluid having a refractive index that is less than 1.6 if LEDs having a plastic body are used.

By way of example, and not limitation, Examples of the present invention will now be given:

EXAMPLE NO. 1

The purpose of the experiment was to determine if LEDs could be run at a high intensity without burning out. 8103 LEDs available from Hewlett Packard were used in a device similar to the apparatus 10 discussed above. The LEDs were cooled with distilled water.

The temperature of the fluid was measured while running the LEDs @90 mA (milliamps). A thermometer was placed in the fluid flow conduits directly before and directly after the LED array.

| Time | Inlet Temperature | Outlet Temperature |
| --- | --- | --- |
| 9:30 | 26° C. | 26° C. |
| 11:00 | 26° C. | 26° C. |
| 11:30 | 26° C. | 26° C. |
| 12:15 | 26° C. | 26° C. |

Note: Water (deionized) was flowing freely into the interior housing of the LEDs. Therefore, no major rise in temperature occurred.

Conclusion: The LEDs held up to large current very well. No ill affects are noticeable. The water did not adversely affect the LEDs, which makes the application feasible.

EXAMPLE NO. 2

Affects of Paratherm NF from Paratherm Corp. on 8103 Array.

The 8103 array was run @50 mA which is equal to the 4.1 volts, measured across the 82Ω resistor, using the Simpson meter.

| Current | Liquid - for cooling LEDs | Peak Wavelength | Intensity mW/cm$^2$ |
| --- | --- | --- | --- |
| 50 mA | None | 660 nm | 14.23 |
| 50 mA | Paratherm NF | 660 nm | 15.32 |
| 50 mA | Calflo | 660 nm | 14.78 |

As indicated above, the fluid increased the intensity of the light generated by the LEDs.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A device for irradiating a product with light of a specific wavelength, the device comprising:

a source of radiation including a plurality of light emitting diodes, the light emitting diodes including a body portion through which radiation is transmitted, the body portion surrounded by a fluid;

a first housing enclosing the light emitting diodes and the fluid thereof, the first housing including a transparent window on an exterior wall of the first housing allowing radiation to flow through the transparent window and to irradiate the product in juxtaposition to the transparent window of the first housing; and a body defining an interior that supports the first housing wherein an opening in the body allows the product to be placed in juxtaposition to the transparent window of the first housing removed from the body.

2. The device of claim 1 further comprising:

a second housing enclosing a second plurality of light emitting diodes, the second housing including a transparent window wherein the second housing is remotely situated such that the product is between the first housing and the second housing.

3. The device of claim 2 wherein the first housing and the second housing are located in planes that are substantially parallel to each other.

4. The device of claim 1 wherein the housing includes an inlet allowing fluid to flow into the interior and an outlet allowing fluid to flow out of the interior.

5. The device of claim 4 wherein the inlet and the outlet are connected to fluid conduits and a pump is provided to pump fluid through a first fluid conduit into the inlet.

6. The device of claim 4 further comprising:

means for cooling fluid before it enters the fluid inlet.

7. The device of claim 1 wherein the fluid is chosen from the group consisting of: distilled water; propylene glycol containing fluids; and oil based fluids.

8. A system for irradiating a container including a product that includes a photoactive agent, the system comprising:

a housing including an interior receiving the container;

a first and second photo diode device on each side of the housing, each photo diode device including a body defining a chamber that includes a plurality of photo diodes generating radiation of a specific wavelength, the chamber including a fluid therein to cool the photo diodes, the first and second photo diode devices located in planes that are substantially parallel to each other and defining a space therebetween in the interior to receive the container wherein the housing includes an opening allowing the container to be placed within the space and removed therefrom.

9. The system of claim 8 wherein the first photodiode device defines a surface for supporting the container.

10. The system of claim 8 further comprising:

means for cooling the fluid.

11. The system of claim 8 wherein each photodiode device includes a fluid inlet and a fluid outlet.

12. The device of claim 8 wherein the fluid is chosen from the group consisting of: distilled water; propylene glycol containing fluids; and oil based fluids.

13. A system for irradiating a container including a product that includes a photoactive agent, the system comprising:

a housing including an interior receiving the container; and a photo diode device including a first body defining a chamber that includes a plurality of photo diodes generating radiation of a specific wavelength, the chamber including a fluid therein cooling the photo diodes, the first body including a transparent window that supports the container when it is placed in the interior of the housing wherein the photo diode device is incorporated into the housing.

14. The system of claim 13 further comprising:

a second body enclosing a second plurality of light emitting diodes, the second body including a transparent window.

15. The system of claim 14 wherein the first body and the second body are arranged substantially parallel to each other.

16. The system of claim 13 wherein the first body includes an inlet allowing the fluid to flow into the interior and an outlet allowing the fluid to flow out of the interior.

17. The system of claim 16 wherein the inlet and the outlet are connected to fluid conduits and a pump is provided to pump the fluid through a first fluid conduit into the inlet.

18. The system of claim 16 further comprising:

means for cooling fluid before it enters a fluid inlet.

19. The system of claim 16 wherein the fluid is chosen from the group consisting of: distilled water; propylene glycol containing fluids; and oil based fluids.

* * * * *